United States Patent [19]

Maltby, Jr. et al.

[11] 4,395,917
[45] Aug. 2, 1983

[54] APPARATUS FOR TESTING GLASS

[75] Inventors: Robert E. Maltby, Jr., Wayne; James T. Sikorski, Rossford, both of Ohio

[73] Assignee: Libbey-Owens-Ford Company, Toledo, Ohio

[21] Appl. No.: 314,574

[22] Filed: Oct. 26, 1981

[51] Int. Cl.³ .................................................. G01N 3/00
[52] U.S. Cl. .......................................... 73/840; 73/838; 65/17
[58] Field of Search ......................... 73/838, 840, 857; 65/17

[56] References Cited

U.S. PATENT DOCUMENTS 3,736,794  6/1973  Biondi .................................... 73/838

FOREIGN PATENT DOCUMENTS 215584  6/1968  U.S.S.R. ............................... 73/838

*Primary Examiner*—Howard A. Birmiel
*Attorney, Agent, or Firm*—Collins, Oberlin & Darr

[57] ABSTRACT

Apparatus for the destructive testing of glass sheets. The sheets to be tested are subjected to a differential pressure condition by establishing a vacuum on one side thereof and lowering the pressure on such side until the glass deflects to its breaking point. The vacuum system includes a control circuit which enables lowering the pressure in a controlled linear manner with time. The apparatus is designed to permit selection of and testing of sheets substantially immediately after the capping operation.

7 Claims, 5 Drawing Figures

APPARATUS FOR TESTING GLASS

BACKGROUND OF THE INVENTION

The present invention relates to an apparatus for the destructive testing of sheet material and more particularly relates to apparatus for determining the strength of glass, particularly heavy glass, i.e., glass intended for architectural applications normally having a thickness of at least 0.125 inch and generally 0.250 inch and above.

It is important that the architect and engineer have at their disposal accurate information as to the strength of glazing materials, for example, an indication or measure of the wind load strength of the material in a desired range of thicknesses. The ability of glass to meet strength specifications is determined, in accordance with one procedure, by selecting samples and ascertaining the load required to break the sheet. Heretofore, this has been accomplished by selecting samples after the glass has been put in storage, and placing these samples in a testing apparatus located near the storage area but remote from the end of the manufacturing line, i.e., the capping area.

Since the testing facility is remote from the capping area and the glass is selected from storage, there is generally a considerable period between the time the glass is made and the time it is tested. Consequently, it has not been unusual to lose as much as one or two days of glass production due to the delay in discovering that the glass does not satisfy code requirements.

SUMMARY OF THE INVENTION

It an object of the present invention to provide an improved apparatus for the destructive testing of glass sheet material.

A further object of the present invention is to provide a glass testing apparatus which enables an accurate determination of glass strength within an extremely short period of time after its manufacture.

Another object of the invention is the provision of a relatively simple yet highly dependable apparatus for indicating the wind load strengh of glass glazing units.

More particularly, it is a further object of the invention to provide a glass testing apparatus in which a glass sheet is subjected to a differential pressure condition by establishing a vacuum on one side thereof and lowering the pressure on such side in a controlled linear manner with time until the glass deflects to its breaking point. The degree of vacuum existing at the time of failure is theoretically equivalent to a wind load at the opposite side or surface and this determines whether the glass meets code requirements.

Other objects and advantages will in part be apparent and will in part appear hereinafter.

For a better understanding of the nature and objects of the invention, reference should be had to the following detailed description and the accompanying drawings.

DESCRIPTION OF THE PREFERRED EMBODIMENT

Figure 1:
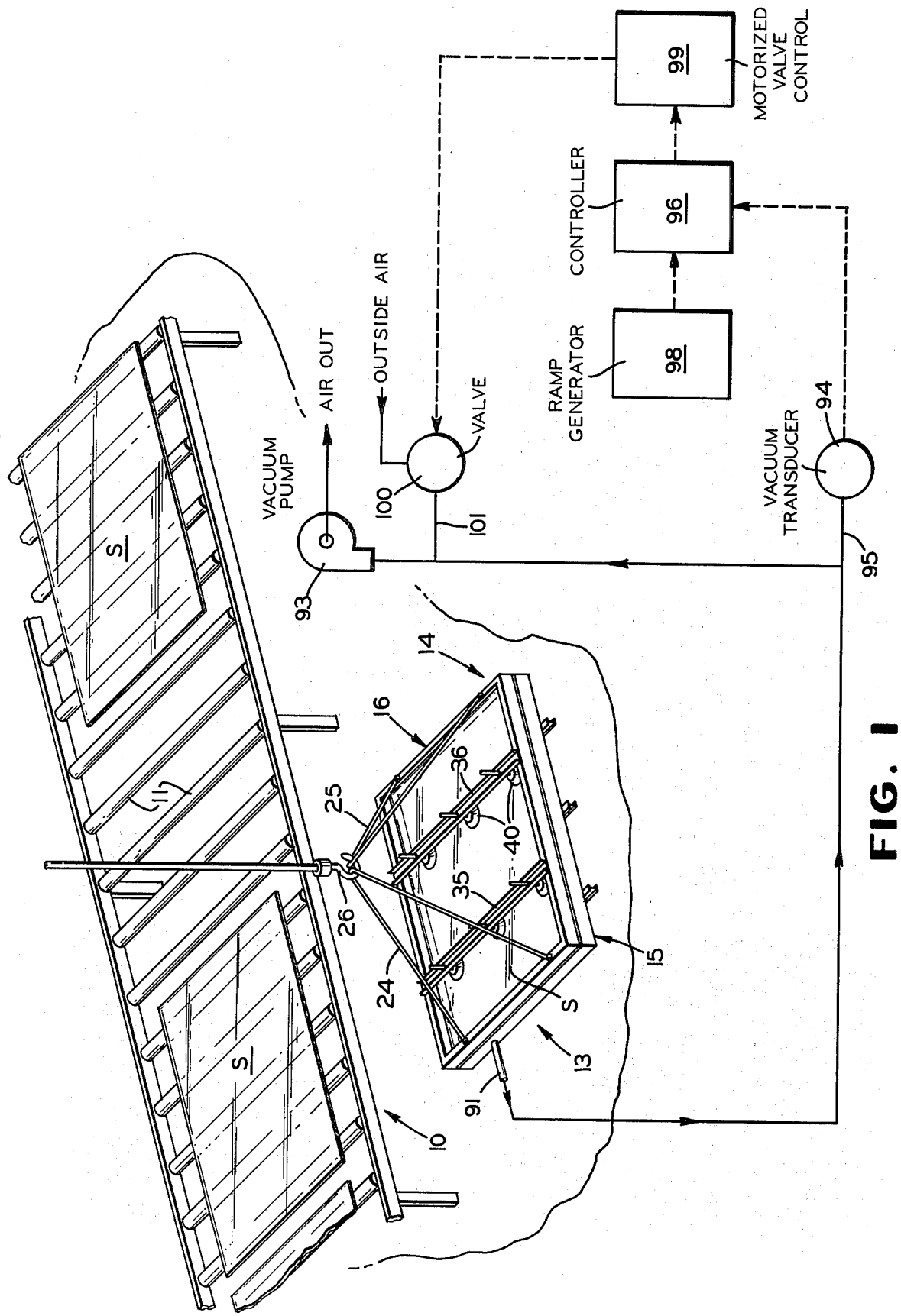
FIG. 1 is a diagrammatic view of the glass testing apparatus of the invention including the control circuit therefor.

Referring now to FIG. 1, reference numeral 10 represents a roll out conveyor comprising a plurality of rolls 11 upon which glass sheets S proceed from a capping area to an area from which they are removed either to a wareroom for storage or to facilities at which they are further processed, for example, cutting, tempering or shipping locations. In accordance with the invention, a sheet is taken at random from the conveyor and subjected to a destructive testing procedure, with the testing apparatus, indicated generally at 13, being designed such that it can be placed directly adjacent the capping area. In this manner the glass sheet or blank S can be removed from the line and immediately tested to determine whether the glass manufactured only a short time before meets the required standards for strength.

The testing apparatus includes an upper or glass handling section indicated generally at 14 and a lower or vacuum box section indicated at 15. The upper section comprises a rectangular frame 16 of a size corresponding to that of the glass sheets leaving the capping area, generally 8 feet by 10 feet, and composed of two transverse or end channel members 17 and 18 and two longitudinally extending side channels 19 and 20 welded together at their respective ends. Pairs of opposed ears or lugs 21 and 22 are welded or otherwise secured to the top flange of the end channels 17 and 18 adjacent the ends of the channels and receive pivot pins 23 and the looped ends of rigid hoisting cables 24 and 25. In this manner the upper section 14 may be carried by an overhead crane or other lifting device (not shown) having a hook 26 depending therefrom.

The rectangular frame 16 also includes angles 30, one leg of each of which is welded to the webs of the end and side channels such that the remaining legs provide an outwardly projecting rim 31 extending about the periphery of the frame. A pair of truncated pyramidal aligning cups 32 and 33 each having an opening 44 in its smaller base are affixed on the rim 31 approximately at the midpoint of the length of each end channel 17,18 by brackets 34. The function of these aligning cups will become apparent as the description proceeds. A gasket 45 is secured to the lower surfaces of the bottom flanges of the end and side channels to provide a peripheral abutment surface for the glass sheet carried on the frame 16 when the latter is brought into operative engagement with the vacuum box section 15.

A pair of cross beams 35 and 36 extend between the side channels 19 and 20 and are welded to the upper flange surface of the channels. The beams 35,36 are disposed in substantially parallel relationship to the end channels 17 and 18 and are spaced apart a distance sufficient to provide good weight distribution of a glass sheet to be carried by the frame 16. In this connection, each of the beams 35,36 has affixed to its lower surface three bushings 37 (FIG. 4) equally spaced along the beam and each surrounding an aperature 38 in the beam. Each bushing is adapted for telescopically receiving a hollow rod 39 supporting a vacuum or suction cup 40. The cup 40 normally is biased away from its respective bushing 37 by a spring 41 disposed on the hollow rod 39 between the bushing and cup. Downward biasing movement of the cups 40 is limited by a collar 42 affixed to the upper end of each rod 39. The collar also provides a fitting for a flexible hose 43 connected to a suitable source of vacuum (not shown). Thus, a vacuum force is established through each of the hoses 43 and the hollow rods 39 to the several cups for securing and holding a glass sheet S onto the frame 16.

The lower or vacuum chamber section 15 of the testing apparatus comprises a rectangular frame 50 of the same size and shape as the upper frame 16. The frame 50 is composed of end channel members 51 and 52 and two side channels 53 and 54 welded to the end channels at their respective ends. Four angles 55 are secured to these channels by welding a leg 56 thereof to the webs of the channels adjacent their upper ends such that the remaining legs provide an outwardly projecting rim 57 extending about the periphery of the frame 50. A plate 60 is secured as by welding to the upper surfaces of flanges 61 of the end channels 51,52 and side channels 53,54 to provide an air impervious bottom wall for the frame 50. A number of transversely extending I-beams 62 are secured through shims or spacers 63 to the underside of the plate 60 at substantially equally spaced intervals along the longitudinal dimension of the frame 50. These beams provide a suitable floor support for the vacuum box section 15 of the apparatus.

A gasket 65 is permanently affixed to the upper surfaces of the flanges 66 of the end channels 51,52 and side channel 53, for example by a suitable adhesive. In addition, a gasket 67 is removably attached to the upper surface of the flange section 66 of side channel 54 by a flexible magnetic strip 68 permanently adhered to the gasket 67. In this manner, the gasket 67 can be removed at selected times from the flange 66, for example when it is desired to dump the vacuum box section 15 to rid it of collected glass cullet. The gaskets 65 and 67 provide a peripheral support for a glass sheet S when the latter is deposited on the vacuum section by the glass conveying section 14, and through the weight of the glass and suitable clamping mechanisms next described enable a substantially fluid tight support relative to the vacuum section.

In the above connection, a number of C-clamps 70 are pivotably attached to the rim 57 at spaced locations about the entire periphery of the bottom section frame 50. These clamps, when swung into their operative position, engage the rim 31 of the upper frame section 16 and when tightened essentially seal the glass sheet between the gaskets 45, 65 and 67 to enable a vacuum to be drawn in the lower section 15.

In order to properly position the glass handling section 14 on the vacuum box section 15, rods 75,76 are secured to the end channels 51 and 52, respectively, by means of brackets 77 and stiffening bars 78. The rod 76 is slightly longer than the rod 75, e.g., longer by an amount just greater than the depth of the aligning cups 32 and 33, such that contact of the rod 76 with the aligning cup 33 on the upper section 14 is made prior to contact of the aligning cup 32 with the rod 75. This construction enables one man, for example operating a portable remote control panel for the overhead crane, to guide the top section 14 into proper alignment and engagement with the vacuum section 15 since he can first mate the rod 76 and the cup 33 while maintaining the sections themselves and the cup and rod 75 and 32 out of contact, and then move to the other side and align cup 32 with rod 75 prior to bringing the sections into actual engagement. This rather than the agonizing procedure of trying to bring both cups and rods into the necessary alignment from one side of the apparatus.

As hereinbefore mentioned, it is necessary to dump the bottom or vacuum box section 15 of the testing apparatus to rid it of cullet after a glass sheet or a number of glass sheets have been destructively tested. For this purpose a pair of clevises 80 (only one of which is shown) are bolted to the floor and receive studs 81 welded to the webs of the two outwardly disposed I-beams 62 of the section 15. The studs 81 are provided with apertures to receive the pivot pins 82 of each clevis. A dumping lug 83 is welded to the side channel 53 and the top flange of the center I-beam 62. The lug 83 has an aperture 84 provided therein for receiving the hook 26 when it is desired to dump the lower section. Raising the hook 26 thus pivots or tips the lower vacuum box section 15 into the position shown in dotted line in FIG. 5 whereby cullet in this section is dumped into a disposed bin 85 provided in the floor.

Figure 5:
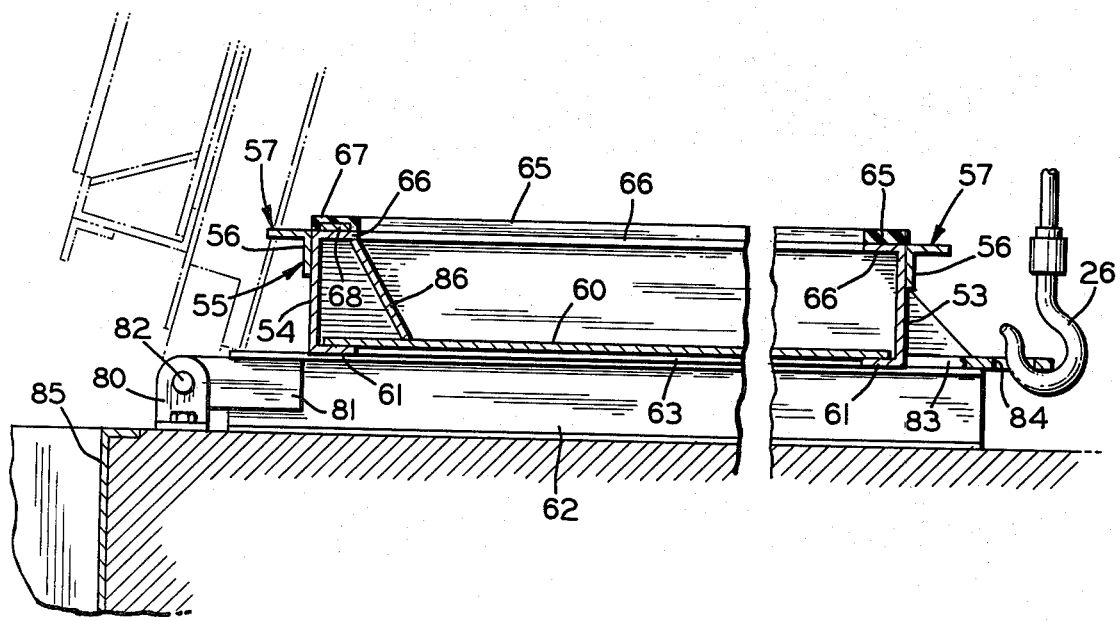
FIG. 5 is a broken, vertical, sectional view taken through the center of the bottom section of the apparatus with the dumping position of a portion of the section shown in broken lines.

To facilitate ridding the vacuum box section 15 of cullet, a plate 86 is inserted at an angle to the bottom plate 60 and welded to the plate 60 and the end of the upper flange of the side channel 54 (FIG. 5). This prevents cullet from accumulating in the bottom corner of the section 15 adjacent the side channel 54 when a dump is proceeding. In this same connection, prior to the dumping procedure the gasket 67 is removed from the top flange of the side channel 54 to prevent it from becoming ripped and torn by the cullet passing thereover.

An opening 90 is provided in the web of the end channel 51 to enable a vacuum line 91 to communicate with the interior of the vacuum box section 15. The line 91 is affixed to the end channel 51 through a collar 92 and to a vacuum pump 93 and control circuit therefor. The control circuit includes a vacuum transducer 94 which senses the pressure in the vacuum box through a line 95 connected with the line 91 and relays this information to a controller 96. A ramp generator 98 is provided on which the desired rate of evacuation of the section 15 is set and this set point signal is fed to the controller 96. The controller 96 takes the signals from the ramp generator and the vacuum transducer and, through a timing mechanism, determines the actual rate of evacuation and compares this rate with the ramp set point. The controller then provides a signal to a motorized valve control 99 which functions to operate a bleeder valve 100 controlling the amount of outside air added to the system through a line 101. In this respect, the valve 100, depending upon the actual rate of evacuation, will close faster or slower as the case may be and thus determine the amount of air being withdrawn from the vacuum box section 15 by the pump 93.

Figure 2:
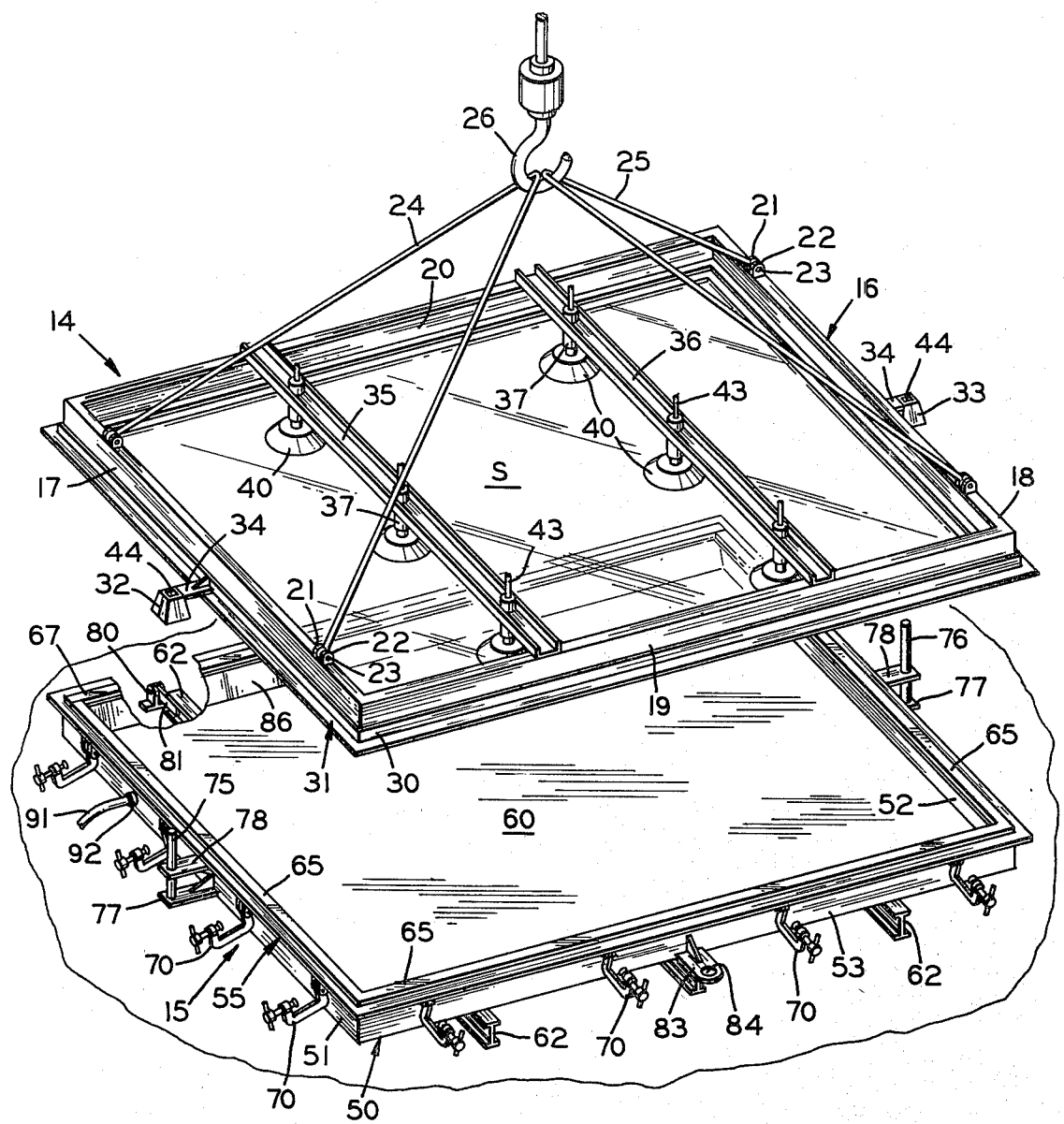
FIG. 2 is a perspective view of the apparatus with certain parts broken away, showing the top or glass pick up section separated from the bottom or vacuum box section.
Figure 3:
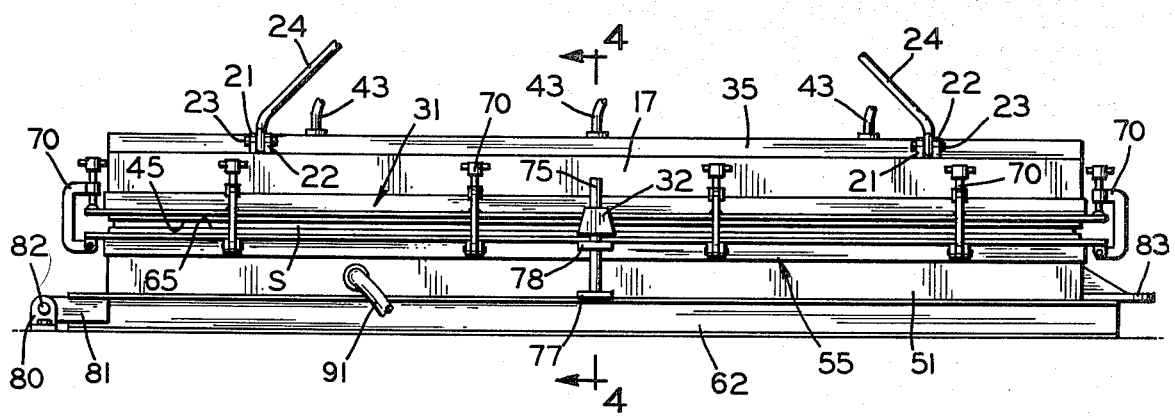
FIG. 3 is a side elevational view of the apparatus with the sections clamped together.
Figure 4:
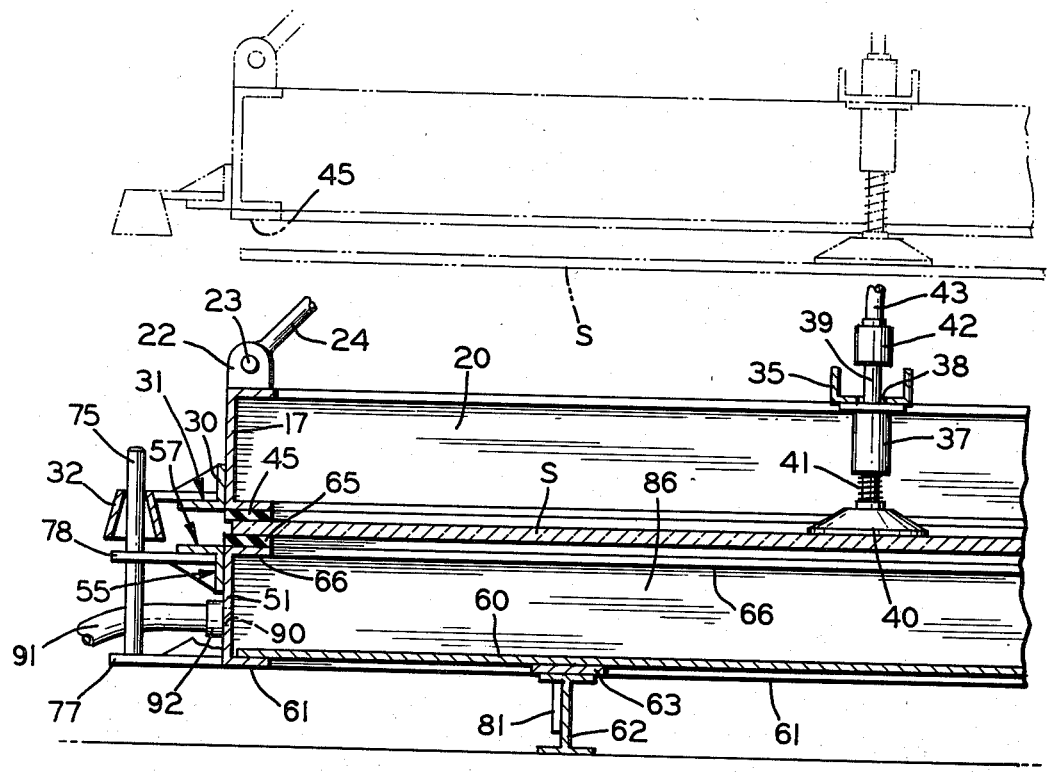
FIG. 4 is an enlarged, fragmentary, vertical, sectional view taken along the line 4—4 of FIG. 3 with a separated position of the top section shown in broken lines.

In operation, a glass sheet S to be destructively tested is periodically removed from the conveyor 10 by positioning the frame 16 of glass handling section 14 squarely over the sheet and bringing the vacuum cups 40 into engagement therewith. A vacuum is drawn through the cups 40 to hold the sheet in engaged position as the frame 16 is lifted and directed towards the lower vacuum box section 15 (FIG. 2 and dotted line position of FIG. 4). The operator brings the section 14 into engagement with the vacuum box section 15 by first nesting the rod 76 loosely in the cup 33 and then moving to the other side of the apparatus and bringing the rod 75 into alignment with cup 32 and lowering the section 14 until the sheet S rests upon the gaskets 65 and 67 of the lower section 15. In this respect, the weight of the upper section acting against the bias of the springs 41 functions to gently cushion the glass as the sections 14 and 15 move into contact with each other. The hook 26 is then removed from the cables 24 and 25 and the vacuum force to the cups 40 discontinued. If desired, fluid under pressure can also be directed to the cups 40 through the same lines establishing the vacuum and is operative to remove a sheet of glass from the cups in the event the weight of the sheet is not sufficient in this regard.

The C-clamps 70 are pivoted upwardly and tightened against the rim 31 around the periphery of the frame 16 such that the glass sheet S is drawn into an essentially airtight seal with the gaskets 65,67.

To operate the test apparatus to accurately predict whether the glass sheets coming out of the capping area meet the required standards for strength, it is necessary that a vacuum is drawn in the vacuum chamber section 15 to provide a linear decrease in chamber pressure with time. A rate of two (2) inches water column per minute has been selected and this rate is set on the ramp generator 98. The bleed valve 100 is set to full open position such that the pump 93 when first started pulls only outside air with substantially no air being removed from the vacuum section 15. In this connection, the pump 93 in this specific example has a capacity of pumping down from zero (0) inch water column to eighty (80) inches water column which has been found sufficient to cause glass breakage in the heaviest glass it is desired to test, i.e., ¾ inch thick, 8 feet by 10 feet sheets. With the pump started and the valve set full open the vacuum transducer 94 senses atmospheric pressure in the section 15 chamber and signals the controller 96 accordingly. The controller in turn sends a signal to the motorized valve control 99 to begin closing the valve 100. The valve closes until the rate of two (2) inches water column per minute is obtained and this rate is maintained through operation of the control circuit until glass breakage occurs. The degree of vacuum at the point of fracture is noted and this information correlated with established strength data to arrive at a value for the particular sheet.

While a single, preferred embodiment of the invention has been illustrated and described in substantial detail, the present invention is not to be considered limited to the precise construction shown. Various adaptations, modifications, and uses of the invention will occur to those skilled in the art to which the invention relates and the invention is to cover all such adaptations, modifications, and uses coming within the spirit or scope of the appended claims.

We claim:

1. Apparatus for the destructive testing of glass sheets, comprising a vacuum chamber defined in part by a base and side walls extending upwardly from the base, gasket means at the top of said side walls for supporting a glass sheet to be tested about the periphery thereof in fluid tight relationship with said side walls, a vacuum pump communicating with the interior of said vacuum chamber, and a control circuit for said vacuum pump, said control circuit including means for establishing a predetermined evacuation rate for said chamber and means for providing a linear decrease in chamber pressure with time.

2. Apparatus for the destructive testing of glass sheets, comprising a vacuum chamber defined in part by a base and side walls extending upwardly from the base, gasket means at the top of said side walls for supporting a glass sheet to be tested about the periphery thereof in fluid tight relationship with said side walls, a vacuum pump communicating with the interior of said vacuum chamber, said vacuum pump having a capacity sufficient to lower the pressure in said chamber to cause deflection of said sheet in direction of the interior of said chamber until breakage of the sheet occurs, a control circuit for said vacuum pump, said control circuit including means for establishing a predetermined evacuation rate for said chamber and means for providing a linear decrease in chamber pressure with time, and means to indicate the degree of vacuum at the moment of glass fracture.

3. Apparatus for the destructive testing of glass sheets, comprising a vacuum chamber section defined in part by a base and side walls extending upwardly from the base, gasket means at the top of said side walls adapted for supporting a glass sheet to be tested about the periphery thereof in fluid tight relationship with said side walls, a glass conveying section including a frame having an outline of substantially the same size and shape as the vacuum chamber section and adapted for removing said sheet to be tested from a conveyor and positioning same on said gasket means, a plurality of vacuum cups mounted within said frame for holding said sheet during conveyance thereof on said frame, means associated with said vacuum chamber section for clamping said conveying section thereto when said sheet is positioned on said gasket means, a vacuum pump communicating with the interior of said vacuum chamber, said vacuum pump having a capacity sufficient to lower the pressure in said chamber to cause deflection of said sheet in the direction of the interior of said chamber until breakage of the sheet occurs, and means to indicate the degree of vacuum in said chamber at the moment of glass fracture.

4. Apparatus as claimed in claim 3, including cooperating means on said vacuum chamber section and said glass conveying section for accurately aligning said sections in a desired orientation prior to clamping thereof.

5. Apparatus as claimed in claim 4, wherein said cooperating means include a pair of aligning cups on opposite sides of said conveying section and a pair of rods on opposite sides of said vacuum section adapted for receipt in said cups, one of said rods being longer than the other to require mating of said longer rod in its corresponding cup prior to mating of the shorter rod.

6. Apparatus as claimed in claim 3, wherein said vacuum chamber section rests on a floor adjacent said conveyor, pivot means on said floor, and means affixed to said vacuum chamber section for pivotal attachment to said pivot means, whereby dumping of broken glass from said vacuum chamber section can take place during pivotal movement thereof.

7. Apparatus as claimed in claim 3, including spring means for biasing said vacuum cups below the plane defined by said frame outline.

* * * * *